United States Patent [19]

Johnson

[11] Patent Number: 4,623,748

[45] Date of Patent: Nov. 18, 1986

[54] DIALKYL ADIPATE LUBRICANTS PREPARATION USING TANTALUM (V) HALIDE/OXIDE-INORGANIC OXIDE CATALYSTS

[75] Inventor: Thomas H. Johnson, Houston, Tex.

[73] Assignee: Shell Oil Company, Houston, Tex.

[21] Appl. No.: 704,984

[22] Filed: Feb. 25, 1985

[51] Int. Cl.[4] .............................................. C07C 67/08
[52] U.S. Cl. ........................................ 560/204; 252/9;
502/60; 502/84; 502/246; 502/354; 560/190
[58] Field of Search ..................... 560/190, 204; 252/9;
502/60, 84, 246, 353, 354

[56] References Cited

U.S. PATENT DOCUMENTS

| | | | |
|---|---|---|---|
| 1,993,736 | 3/1935 | Graves et al. | 560/190 X |
| 1,993,737 | 3/1935 | Graves et al. | 560/190 X |
| 1,993,738 | 3/1935 | Graves et al. | 560/190 X |
| 2,499,848 | 3/1950 | Catlin et al. | 560/190 |
| 2,614,128 | 10/1952 | Mertzweiller | 560/190 X |
| 2,792,417 | 5/1957 | Dean | 560/190 X |

*Primary Examiner*—Natalie Trousof
*Assistant Examiner*—Vera C. Clarke

[57] ABSTRACT

This invention relates to a process for converting propylene/butylene oligomers to dialkyl adipates where said adipates have higher flash points than conventionally prepared adipates.

4 Claims, No Drawings

DIALKYL ADIPATE LUBRICANTS PREPARATION USING TANTALUM (V) HALIDE/OXIDE-INORGANIC OXIDE CATALYSTS

FIELD OF THE INVENTION

This invention relates to improved dialkyl adipate lubricants and the process for preparing them.

BACKGROUND OF THE INVENTION

A dibasic acid ester as is normally used as a synthetic lubricant base stock is an ester of a straight-chain dibasic acid, such as adipic, azelaic or sebacic acid, and a long-chain branched primary alcohol usually having eight to thirteen carbon atoms. The alcohol typically utilized is an "oxo" alcohol. See, for example "Synthetic Lubricants", Report No. 125, Process Economics Program, May, 1979, pp. 105 et seg., SRI International.

The Dimersol Process is a catalyzed liquid phase oligomerization of lower olefins, particularly propylene and butylene. The catalyst is formed by reacting a nickel compound with a hydrocarbyl aluminum halide. The primary product is the dimer with smaller amounts of the trimer and tetramer being present. General discussion of the Dimersol Process can be found in *Hydrocarbon Processing*, Vol. 89, pp 143–149, May, 1980 and Vol. 91, pp 110–112, May, 1982. The higher oligomers are quite useful for converting to alcohols and reacting with adipic acid to form adipate esters which are useful as lubricants. The instant invention relates to a process to enhance and augment the higher olefin oligomers whereby when they are converted to adipate esters, said esters have improved properties.

SUMMARY OF THE INVENTION

This invention relates to dialkyl adipates which are useful as lubricants. They are prepared by reacting or "reforming" the propylene or butylene oligomer products from a Dimersol Process in the presence of a tantalum (V) halide/oxide-inorganic oxide catalyst, converting the resulting $C_8$ olefin, $C_9$ olefin, and/or $C_{12}$ olefin to a $C_q$, $C_{10}$ and/or $C_{13}$ alcohol and reacting the alcohol with adipic acid to produce the dialkyl adipate. The adipates thus prepared have higher flash points than adipates prepared from conventional oxo alcohols. Since flash points are an indication of evaporative loss that would be expected in the use of lubricants, higher flash points are therefor indicative of longer operational life.

DESCRIPTION OF THE PREFERRED EMBODIMENT

In this invention, a Dimersol oligomer product is contacted with a tantalum (V) halide/oxide-inorganic oxide catalyst, the resulting "reformed" olefins hydroformylated to alcohols and the alcohols reacted with adipic acid or a derivative of adipic acid to produce the dialkyl adipate.

The Dimersol Process is a catalyzed liquid phase oligomerization, primarily dimerization, of propylene or butylene. The process was developed by the Institute Francais du Petrole. The process uses generally a catalyst prepared by reacting a nickel compound with a hydrocarbyl aluminum halide. Illustrations of the catalyst that can be used in this type of process are given in U.S. Pat. No. 4,366,087, issued Dec. 28, 1982, U.S. Pat. No. 4,362,650, issued Dec. 7, 1982 and U.S. Pat. No. 4,398,049, issued Aug. 9, 1983. The Dimersol Process produces primarily dimers with smaller amounts of trimers and tetramers as well as higher oligomers. An illustrative example of the products of this type of process is shown in Examples 6 and 10 of U.S. Pat. No. 4,398,049 wherein propylene and butylene are oligomerized to produce 85% of the dimer, 12% of the trimer and 3% of the tetramer. In general, the product of the Dimersol oligomerization of propylene or butylene will result in a product comprising about 75–85% by weight of dimers, 9–15% by weight of trimers, 1–5% by weight of tetramers and less than 2% by weight of the higher oligomers.

The octenes, nonenes and/or dodecenes present in the oligomerization product can be hydroformylated to produce alcohols which then provide very suitable reactants for preparing lubricants such as the dialkyl adipates. There are, however, certain problems in doing this directly with the oligomers from the Dimersol Process. The dodecenes from the Dimersol Process are highly branched and do not hydroformylate as readily as olefins not so highly branched. Further, the dodecenes from the Dimersol Process comprise only a very small amount of the total product, which in many cases would not justify the expense of attempting to process these materials for use in preparing lubricants. It has been found that by reacting the Dimersol product with the catalyst as hereinafter described which is a tantalum (V) halide/oxide-inorganic oxide material, the octene and nonene products of the Dimersol Process are enhanced for hydroformylation because the more highly branched materials are oligomerized out into higher oligomers and the dodecenes are augmented by the oligomerization of the lower carbon number materials present in the Dimersol product being oligomerized. The use of the tantaum (V) halide/oxide-in organic oxide catalyst to "reform" the Dimersol product results in $C_8$, $C_9$ and/or $C_{12}$ olefins that when hydroformylated to alcohols and reacted with adipic acid produce dialkyl adipates with superior properties to that of adipates from conventional oxo alcohols.

As used herein, the term "viscosity index" (VI) refers to the sensitivity of a lubricant's viscosity with change in temperature and is measured by ASTM D-2270. "Pour point" refers to the temperature at which a lube no longer flows and is measured by ASTM D-97. "Flash point" is an indirect measure of volatility and is measured by ASTM D-92. "Kinematic viscosity" refers to the flow property of a material at a defined temperature and is measured by ASTM D-445.

The key to producing the compositions of the instant invention resides in the use of the tantalum (V) halide/oxide-inorganic oxide catalyst to reform the propylene and/or butylene oligomers to produce octenes, nonenes and/or dodecenes which are hydroformylated to alcohols and reacted with adipic acid. The exact chemical make-up of the reformed octenes, nonenes amd dodecenes are difficult if not impossible, to determine with conventional analytical techniques due to the number of isomers present.

The catalysts used to prepare the composition of the instant invention comprises pentavalent tantalum, (also written as tantalum (V)), halogen (or halide), oxygen (or oxide) and a solid inorganic oxide substrate wherein at least one valence of tantalum is bound to oxygen, which oxygen is bound to the substrate, at least one valence of the tantalum is bound to the halogen and the remaining tantalum valences are bound to halogen and/or oxygen, which oxygen may or may not be bound to the substrate. The halogens are fluorine, chlorine, bromine, iodine and mixtures thereof. Preferred halogens are fluorine and chlorine.

The inorganic oxides that are useful as substrates to prepare the catalyst are those inorganic oxides which have hydroxyl groups attached to the surface of the substrate. The hydroxyl groups provide the means by which the tantalum pentahalides are bound by reaction to the surface of the substrate. The score is broad and any metal or semi-metal oxides which have surface hydroxyl (or oxyhydroxyl) groups can be utilized in preparing the catalysts.

The term "inorganic oxide", although used herein in the singular tense, is meant to include the single oxides such as silica, or alumina as well as plural and complex oxides such as silica-alumina, silica-alumina-thoria, zeolites and clays. The term "semi-metal" is a term referring to the semi-conductor materials like silicon, germanium etc., although in the catalyst art, the semi-metal oxides are frequently encompassed with the term "metal oxide".

The preferred inorganic oxide substrate used to prepare the catalysts are the porous solid inorganic oxides which contain surface hydroxyl groups and which are conventionally used as catalysts and catalyst supports. Non-limiting examples of these types of materials include those having a major component of silica or alumina or both, such as, for example, alumina and aluminous materials, silica and siliceous materials; clays, particularly open lattice clays; and crystalline aluminosilicates (zeolites). Non-limiting examples of aluminous and siliceous materials include, for example, silica-alumina, silica-magnesia, silica-zirconia, silica-titania, alumina-chromia, alumina-ferric oxide, alumina-titania as well as ternary compositions such as, for example, silica-alumina-titania, silica-alumina-zirconia, etc. Non-limiting examples of crystalline aluminosilicates useful as substrates include synthetic zeolites such as, for example, A, X, Y, L and ZSM types such as ZSM-5 and others and naturally occurring zeolites, such as erionite, faujasite, mordenite, sodalite, cancrinite and others. Non-limiting examples of open lattice clays useful as substrates include bentonite, montmorillonite and others. In a preferred embodiment, the metal oxide should have a major component of silica or alumina or both.

Particularly suitable as substrates for preparing the catalysts are those solid inorganic oxide compositions known as metal or semi-metal oxide gels or gel oxides. The gel oxides which are particularly suitable for use in preparing the catalysts are any of the oxide gels that are well known in the catalytic art useful as either catalyst base materials or as supporting materials in catalyst compositions. Additionally, the term "metal or semi-metal oxide gel" or "gel oxide" as used herein shall also include the plural oxide gels, i.e., those that contain mixtures or compounds of two or more metal oxides. A metal or semi-metal oxide gel is basically a metal or semi-metal oxide that contains chemically bound water in the form of hydroxyl groups or oxyhydroxyl groups as opposed to adsorbed water and water of hydration, although adsorbed water and water of hydration may also be present. They are typically prepared by the precipitation of the metal or semi-metal component(s) in an aqueous medium. Upon calcination at sufficiently elevated temperatures, water is given off and the gel is converted to the oxide with two hydroxyl moieties giving one molecule of water and an oxygen is attached to a metal ion. Illustrative of gel oxide base materials used to prepare the catalysts are aluminas, silicas, alumina-silicas, alumina-zirconias, silica-zirconias and the like, including naturally occurring hydrous oxide materials such as clays, such as, for example, the kaolinites, the montmorillonites and the like. Among the clays the open lattice clays are particularly desirable. Also included are the zeolites, both natural and synthetic. The structure of the gel oxides can range from amorphous to highly crystalline. Preferred oxide gel materials are selected from the group consisting of alumina, silica, alumina-silica, crystalline alumino-silicates (zeolites) and open lattice clays.

Since the tantalum (V) halide/oxide is bound to the surface of the inorganic oxide substrate by a reaction of tantalum pentahalide with the inorganic oxide substrate through a hydroxyl moiety, the inorganic oxide substrate must have pendant surface hydroxyl groups attached to the surface. Before reaction, the inorganic substrate must have pendant surface hydroxyl groups, whereas, after reaction, the inorganic oxide substrate may or may not have surface hydroxyl groups, depending on the degree of reaction with the tantalum pentahalide.

Prior to use in preparing the catalysts the hydroxyl-containing inorganic oxide substrate should be substantially free of absorbed water, i.e., "substantially dehydrated or anhydrous". The absorbed or free water is removed by heating the substrate at temperatures ranging from about 100° C. to about 900° C. prior to contact with ythe tantalum pentahalide vapor. Any environment that provides for drying is suitable such as air, vacuum, inert gas such as nitrogen, etc. The dried metal oxide substrate should be kept away from a humid atmosphere after drying. It is understood that a dried inorganic oxide substrate prior to use in preparing the catalysts will still contain chemically bound water in the form of hydroxide and oxyhydroxide.

An aluminum oxide gel is one of the preferred substrates. This alumina can be any of the variety of available aluminas. These are commercially available under various names such as alumina gels, activated aluminas, gamma aluminas, etc. Regarding purity of the alumina, it may be stated that small amounts of impurities are not generally detrimental, and may be beneficial when the impurity is present as a co-gel. In fact "impurities" may be purposely added for catalytic effects.

The following table lists several commercial aluminas and their properties which are found suitable.

| Alumina | Surface Area, m$^2$g | Pore Vol., cc/gm | Na, ppm | SO$_4^=$, % wt | Fe$_2$O$_3$ % wt | Cl$^-$, % wt |
|---|---|---|---|---|---|---|
| CCI[a] | 252 | 0.8 | 160 | 0.06 | — | 0.02 |
| KA-201[b] | 365 | 0.42 | 600 | 0.03 | — | 0.01 |
| RA-1[c] | 263 | 0.26 | 4700 | 0.02 | 0.18 | — |
| ACCO[d] | 225 | 0.68 | 580 | 0.6 | — | 0.6 |
| Norton | 218 | 0.62 | 51 | 0.03 | — | 0.03 |

[a]Catalysts & Chemicals, Inc., now United Catalysts
[b]Kaiser
[c]Reynolds Corporation
[d]American Cyanamid Corporation
[e]Conoco Corporation
[f]Filtron Corporation Silica gel is also another preferred substate. These are readily available commercially and are essentially substantially dehydrated amorphous silica. These materials are available in various density grades, from low density with surface areas ranging from about 100–300 m$^2$/g to regular density with surface areas up to about 800 m$^2$/g. The commercially available materials are used as dessicants, selective absorbents, catalysts and catalyst supports. Regarding purity of the silica, it may be stated that small amounts of impurities are not generally detrimental and may be beneficial when the impurity is present at a co-gel. In fact, "impurities" may be purposely added for catalytic effects. The following table lists several commercial silicas and their properties which are found suitable.

| Support | Surface Area, m$^2$/g | Pore Vol., cc/g | Density g/cc | Particle Size |
|---|---|---|---|---|
| Davison* Grade 952 SiO$_2$ | 300 | 1.65 | 0.35 | 70 mesh (avg) |
| Davison Grade 59 SiO$_2$ | 300 | 1.15 | 0.38 | 8 mesh |
| Davison Grade 57 SiO$_2$ | 300 | 1.0 | 0.4 | 100 mesh |
| Davison Grade 12 SiO$_2$ | 700 | 0.54 | 0.75 | 20 mesh |
| Davison Grade 03 SiO$_2$ | 750 | 0.43 | 0.7 | 8 mesh (avg) |

*Manufactured by Davison Chemical Divison, W. R. Grace & Co.

Other preferred substrates are the aluminosilicates. These materials contain various mixtures of aluminum and are generally employed as cracking catalysts. Typically they contain from about 50 to about 95, preferably from about 70 to about 90 percent by weight of silica. Illustrations of commercially available alumina-silicas are Davison Grade 980-25 (manufactured by Davison Chemical Division, W. R. Grace & Co.) which contains about 75% SiO$_2$ and 25% Al$_2$O$_3$ and Davison Grade 980-13 which contains about 87% Al$_2$O$_3$. These materials can be prepared in a conventional fashion, as for example by co-precipitation, co-gellation, or by spray drying.

Encompassed within the term "aluminosilicates" are most of the zeolites.

The zeolites are found to be specifically useful as substrates. Zeolites are ordered, porous crystalline aluminosilicates having a definite crystalline structure within which there are a large number of small cavities which are interconnected by a number of still smaller channels. Zeolites useful as substrates may be either synthetic or natural. At least 34 species of zeolite minerals are known and the synthetic zeolites number in the hundreds. Any zeolite will be useful as a substrate provided that the zeolite, prior to reaction with tantalum pentahalide, contains chemically bound water in the form of hydroxyl groups. Depending on the state of reaction, the reacted product may contain no hydroxyl groups, if all such groups were reacted with the tantalum pentahalide, or there may be unreacted hydroxyl groups still present.

The techniques for the preparation of the tantalum pentahalide intermediates are well known in the art and typically are prepared by passing a dry halogen gas over tantalum metal at elevated temperatures. By way of illustration, tantalum pentachloride is prepared by passing dry chlorine over tantalum metal at a temperature above 200° C. The tantalum pentahalides utilized will comprise tantalum pentafluoride, tantalum pentachloride, tantalum pentabromide and tantalum pentaiodide.

The gel oxide-tantalum (V) halide/oxide catalysts are prepared by a process comprising reacting under substantially anhydrous and oxygen-free conditions a suitable gel oxide which has water chemically bound as hydroxyl and which is substantially free from absorbed water with tantalum pentahalide vapor and thereafter recovering the product. The metal or semi-metal oxide catalysts thus produced have tantalum (V) halide/oxide bound to the surface thereof. By the term "bound" it is meant herein that the pentavalent tantalum has at least one valence bound to an oxygen which is part of the inorganic oxide substrate. By the term "surface" it is meant both the external and internal pore surfaces which are accessible to the tantalum pentahalide vapor during the preparative process.

The tantalum pentahalides readily sublime and thus lend themselves to a preferred method of preparation which is called "reactive sublimation" wherein tantalum pentahalide is sublimed into an anhydrous, non-oxidizing atmosphere and allowed to contact and react with the hydroxyl-containing metal or semi-metal oxide.

In the preparation of the catalysts, by reactive sublimation, it is important that the reaction be carried out under substantially anhydrous conditions and in a neutral or reducing environment to prevent decomposition of the tantalum halide.

In this preferred method of catalyst preparation, the tantalum pentahalide is sublimed by suitable application of temperature and/or vacuum into an essentially anhydrous and oxygen-free atmosphere where it is allowed to contact and react with a substantially anhydrous, hydroxyl-containing metal or semi-metal oxide substrate. Any temperature and/or vacuum which causes the tantalum pentahalide to sublime is suitable. Temperatures up to about 200° C. are suitable. Frequently the inorganic oxide substrate is heated during the reaction, say up to about 200° C. This heating is not critical to the preparation of catalysts, but it has been found that by so heating, a more even distribution of the tantalum pentahalide on the metal oxide substrate is effected. After reaction, the inorganic oxide composition is frequently subjected to an additional period of time at sublimation conditions without the presence of a tantalum pentahalide source. This extra step allows for any unreacted tantalum pentahalide to be sublimed off of the metal or semi-metal oxide composition. The inorganic oxide substrate before use is frequently subjected to a heat treatment to remove absorbed water. Vacuum can also be applied. Generally, if a pre-treatment temperature is too low, free water will remain, and if the temperature is too high, sintering of the inorganic oxide substrate will occur, both of which can adversely affect the catalytic properties. Generally, the most desirable pretreatment temperatures of the metal oxide substrate range from about 200° to about 400° C.

It is postulated that when tantalum pentahalide reacts with the hydroxyl group of a inorganic oxide substrate, that the reaction may be illustrated variously as follows (using chloride as an illustrative halide):

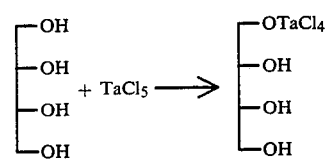

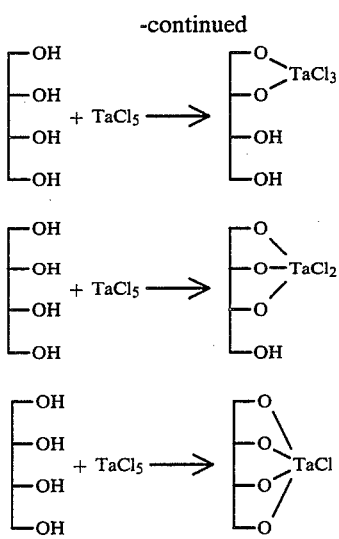

In the final catalyst a mixture of the above described reaction products will exist. The distribution of these reaction products is believed to be affected by reaction conditions, such as temperature. Analysis of chlorine/tantalum ratios in catalysts containing about 8-17% wt. of tantalum show Cl/Ta atomic ratios of from about 2.5:1 to about 3.5 to 1.

Thus, depending on the tantalum content desired in the final catalyst, a tantalum pentahalide vapor is reacted with the hydroxyl-containing metal or semi-metal oxide substrate until a part or the whole or the hydroxyl group population of the metal oxide substrate is exhausted.

The reaction between the tantalum pentahalide vapor and the hydroxyl-containing inorganic oxide substrate is carried out at temperatures ranging from about room temperature to elevated temperatures, say to 150°-200° C. or higher. The reaction is normally carried out in an anhydrous, i.e., free from water vapor, atmosphere. The atmosphere should further be a neutral or reducing atmosphere i.e., oxygen-free. Dispersal of the tantalum pentahalide vapor in a vacuum provides a quite suitable atmosphere for reaction with the metal or semi-metal oxide substrate.

The inorganic oxide-tantalum (V) halide/oxide catalysts may be produced in virtually any physical form, as for example, they may be pellets, beads, extrudates, microspheres and in other particular forms, as for example rings, saddles and the like in porous or non-porous form.

The catalysts basically comprise metal or semi-metal oxide substrates having tantalum (V) halides/oxides reactively bound to the surface of said substrate. The halides are selected from the group consisting of fluoride, chloride, bromide, iodide and mixtures thereof. Preferred halides are fluoride and chloride. The catalysts are generally prepared by a process which comprises contacting the hydroxyl-containing metal or semi-metal oxide substrate in a substantially anhydrous state with tantalum pentahalide in the vapor state and allowing the vapor to react with the substrate in an atmosphere which is substantially oxygen- and water-free. In the preferred process sublimation of the tantalum pentahalide is used to put the tantalum pentahalide in the vapor state. Tantalum pentachloride is the preferred sublimation agent, producing the highest metal loadings on the inorganic oxide substrate.

A variation of the above process is utilized to produce a catalyst containing mixed halides, particularly mixed chlorides and fluorides. In this variation a tantalum (V) chloride/oxide-inorganic oxide composition is prepared by reactive sublimation. The tantalum (V) chloride/oxide-metal oxide composition is then contacted with an oxygen-containing gas or a chemical compound containing oxygen which is weakly covalently bonded to the compound. It is postulated that oxygen replaces part of the halide of the composition. The material is then reacted with a liquid or gaseous fluorinated hydrocarbon which is believed to react preferentially with the oxygen bound only to the tantalum, producing, it is postulated, a composition containing various mixtures of chlorides, fluorides, oxides, oxychlorides, oxyfluorides, oxychlorofluorides, etc., depending on reaction conditions. Analyses of catalysts prepared in this fashion show that they contain varying amounts of chlorine and fluorine along with amounts of oxygen (not bound to the substrate) ranging from insignificant to moderate, depending on the degree of fluorination obtained using the fluorinated hydrocarbon. The amount of oxygen remaining can be varied by choice of fluorinated hydrocarbon and reaction conditions. Reaction temperatures and pressures for the reaction with the fluorinated hydrocarbon are not critical. Temperatures of room temperature or greater are generally suitable. Different fluorinated hydrocarbons will have different optimum temperatures, pressures and times of contact, and these can readily be determined by routine experimentation. Particularly suitable fluorinated hydrocarbons are the Freons, such as for example, Freon 12 ($CF_2Cl_2$), Freon 14 ($CF_4$), Freon 23 ($CHF_3$), Freon 112 ($CCl_2F-CCl_2F$), Freon 116 ($CF_3-CF_3$), Freon 142 (chlor-difluor-methyl methane), Freon C138 (octafluorocyclobutane) and similar materials. One particular advantage of this process is that it allows for the preparation of catalysts containing higher amounts of fluoride than does the process using reactive sublimation of tantalum pentafluoride alone. Compositions containing the fluoride are more resistant to oxygen degradation than the compositoins containing chloride alone. Thus, when the mixed chloride/fluoridecompositions are used as catalysts, the feeds not be purged of oxygen and air is no longer a poison. Feeds containing oxygen (e.g. $O_2$, peroxide, etc.), however, will still complete for catalyst sites and, hence, the observed rates of reaction can be reduced.

As noted above, a modification of the basic catalyst can be obtained by contacting the tantalum (V) halide/oxygen inorganic oxide compositions with oxygen or a compound containing oxygen which is weakly covalently bonded to said compound. Illustrative of said compounds are the peroxides and peroxy compounds, both organic and inorganic, the hypohalide's etc. It is postulated that contact of the catalysts with oxygen or the indicated oxygen-containing compounds converts to part of the halogen on the composition to oxygen which is not bound to the substrate. Thus, there are two possible types of oxygen bound to the pentavalent tantalum of the composition. One type is the oxygen(s) which is bound to the tantalum and to the substrate. The presence of this type of oxygen is required to produce the catalysts. The other type of oxygen which optionally may be present is oxygen bound only to the tantalum of the catalyst composition. Thus, at least one valence of pentavalent tantalum is bound to oxygen which is bound to the substrate, at least one valence of the tantalum is bound to halogen and the remaining tantalum valences are bound to halogen and/or oxygen which is or is not bound to the substrate. This modification contaning the optional oxygen may be effected either inadvertantly or purposefully. It may be effected by contact with oxygen or oxygen-containing compounds present as additives or impurities in feed streams when the compositions are used as catalysts.

The Dimersol product is reacted together in the presence of the tantalum (V) halide/oxide-oxide gel catalyst described herein using conventional techniques, such as a stirred reactor or a packed bed. The reaction temperature generally ranges from about 25° to about 300° C., preferably from about 100° to about 250° C. The product stream direct from the Dimersol process may be contacted with the tantalum-containing catalyst or the Dimersol product stream may be suitably fractionated into $C_8$, $C_9$ and/or $C_{12}$ olefin catalysts which are then contacted with the tantalum-containing catalyst.

Sufficient pressure is required to maintain most of all (at least a substantial portion) of the feed derived from the Dimersol process in the liquid state. Pressures generally range from about 100 to about 1000 psi.

After contact with the above described tantalum (V) halide/oxide-inorganic oxide catalyst, the $C_8$, $C_9$ and/or $C_{12}$ olefins are separated from the reaction mixture by suitable means such as, for example, distillation. The $C_8$, $C_9$ and/or $C_{12}$ olefins are then hydroformylated to provide alcohols.

Hydroformylation is a term used in the art to denote the reaction of an olefin with CO and $H_2$ to produce an aldehyde/alcohol which has one more carbon atom then the reactant olefin. Strictly speaking hydroformylation of an olefin produces an aldehyde. However, in many reaction processes the catalyst utilized to produce the aldehyde also reduces the aldehyde to the alcohol. Frequently, in the art, the term hydroformylation is utilized to cover the aldehyde and the reduction to the alcohol step in total, i.e., hydroformylation refers to the production of alcohols from olefins via carbonlyation and an aldehyde reduction process. As used herein, hydroformulation refers to this production of aldehydes/alcohols from olefins.

The hydroformylation step utilized in the instant process is not unique or critical to the instant invention. Any of the many well-known "oxo" hydroformylation processes can be utilized in the instant process. Various commercial processes have been summarized in SRI International's Process Economics Program Reports, Report No. 27, Linear Higher Alcohols, August, 1967; Report No. 21, Oxo Alcohols, November, 1966; Report No. 21A, Oxo Alcohols, November, 1971; Report No. 21B, Oxo Alcohols, May, 1978. These reports describe the use of various catalysts in a hydroformylation process as well as the detailed aspects of the process. Further descriptions of the oxo process can be found in "Organic Syntheses via Metal Carbonyls, Volume II" edited by I. Wender and P. Pino, John Wiley and Sons, 1977 and in "New Syntheses with Carbon Monoxide" (Reactivity and Structure Concepts in Organic Chemistry, Volume II), edited by J. Falbe, Springer-Verlag, 1980. Illustrative catalysts include cobalt hydrocarbonyl catalyst, cobalt-phosphine ligand catalysts, and rhodium-phosphine ligand catalyst. The choice of catalysts determines the various reaction conditions imposed. One of ordinary skill in the art, by referring to the above-cited references, or any of the well-known literature on oxo alcohols can readily determine those conditions of temperatures and pressure that will be needed to hydroformylate the reformed Dimersol product using the particular catalyst or catalysts involved.

After hydroformylation to the alcohol, the $C_9$, $C_{10}$ and/or $C_{13}$ alcohols are separated from the hydroformylation product by conventional means such as for example, distillation, and reacted with adipic acid or an ester-forming adipic acid derivative to produce the dialkyl adipate lubricant. The dialkyl adipate material is separated from the esterified reaction product by suitable means such as, for example, distillation or fractional crystallization.

The dialkyl adipates can be prepared by several processes. However, only the direct esterification method, where the dibasic acid is reacted directly with the alcohol, is used commercially.

An example of the directly esterification is given below, using adipic acid and tridecyl alcohol.

$HO_2C(CH_2)_4CO_2H + 2C_{13}H_{27}OH \longrightarrow$ adipic acid     tridecyl alcohol

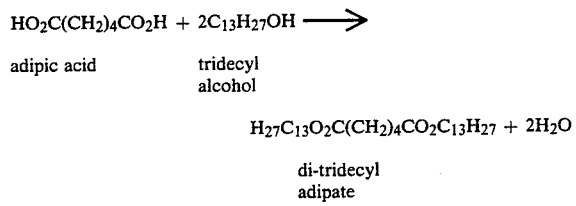

$H_{27}C_{13}O_2C(CH_2)_4CO_2C_{13}H_{27} + 2H_2O$ di-tridecyl adipate

Esterification is an equilibrium reaction and will not go to completion unless the equilibrium is shifted. In the case of the non-volative adipic acid esters, this is accomplished by removal of the more volatile water as soon as it is formed. An azeotroping agent, such as xylene or toluene, can be used to lower the temperature at which water will vaporize. However, as the reaction is carried out at atmospheric pressure and a temperature well above the boiling point of water, but below the boiling point of the ester, an azeotroping agent is not required. Temperatures will range generally from about 100° to about 300° C. Preferred, temperatures are about 150°–200° C.

About 5 to 10% excess alcohol can suitably be used. The alcohol is more volatile than the dibasic acid and can be recovered by distillation, carried out under a vacuum to lower the vaporization temperatures and minimize possible degradation. Any unreacted acid can be neutralized with aqueous sodium carbonates solution.

A catalyst may be used to speed up the esterification, for example, para-toluene sulfonic acid. An excellent summary of the production of the di-tridecyl adipate can be found in SRI International's Progress Economics Program Report No. 125, May 1979, pp. 109 et seq.

Of course, other ester-forming adipic acid derivatives can be utilized to form the adipic esters. Synthesis of esters is an old established process and much literature in the field is available to anyone who wants to synthesize them. For example, in addition to direct esterification described above, esters can be produced from the acid chlorides by direct reaction with the alcohol as well as from alcoholysis of adiponitrile. As used herein, the term "adipic acid derivatives" refers to those derivatives such as adipoyl chloride and adiponitrile which can be used to form the adipic esters. The process of the instant invention is described below by the following illustrative embodiments which are provided for illustration, and are not to be construed as limiting the invention.

ILLUSTRATIVE EMBODIMENT

Catalyst Preparation

The following illustrates a typical preparation of the catalyst used to make the lubricants of the instant invention. Other examples are given in U.S. application Ser. No. 527,535 filed Aug. 29, 1983, now U.S. Pat. No. 4,489,171 issued Dec. 18, 1984, incorporated by reference herein. In this preparative technique a glass scrubbing bottle was modified by internally adding a course fritted disc which divided the bottle into a upper section and a lower section. The lower section was fitted with a stoppered connection which allowed it to be charged with tantalum pentachloride and the upper section was fitted with a vacuum stopcock connection which allowed it either to be closed off or connected to a vacuum. To the modified gas-scrubbing bottle were added about 20 g of $TaCl_5$ to the bottom section and 60 g of Davison 57 silica ($-20+30$ mesh, pretreated at 300° C. under 0.1 torr vacuum for 12-24 h) to the top section. Both sections were loaded in a dry box containing a nitrogen atmosphere. The bottom section was stoppered and top section had the vacuum stopcock closed before removing from the dry box. The bottom section of the bottle was immersed into an oil bath and heated at about 150° C. The top section was wrapped with heating tape and heated to about 150° C. A vacuum (about 0.1 torr) was applied at the top of the bottle. The heating and vacuum phase of the preparation was simultaneous and carried out over a period of 18 h. At the end of 18 h, the bottle (vacuum stopcock closed) was put back into the dry box and 20 g of fresh $TaCl_5$ was added to the bottom section. The rest of the procedure was then repeated for another 18 h. Then the silica was removed, in a nitrogen-filled dry box, and vertically sublimed at 150° C. and torr for 18 h. This step was employed to remove any deposited but unreacted $TaCl_5$ on the silica surface. A small ($<200$ mg) of $TaCl_5$ was generally collected on the cold finger of the sublimator.

Twelve milliliters of the tantalum (V) chloride-silica composition was added to a fixed-bed flow reactor and treated with air at a flow rate of 4 liter/min for 15 minutes at 100 psi and 200° C. The air-treated material was then treated with Freon 12 ($CF_2Cl_2$) at 200° C. and 70 psi at a flow rate of 2.4 liter/hr for 5 hours. The flow tube was then sealed and left under an atmosphere of Freon 12 at 200° C., 75 psi for 60 hours. Analysis of the resultant composition by neutron activation showed it to contain about 15.7%w Ta, 1.9%w Cl and 5.7%w F.

LUBRICANT PREPARATION

Catalytic "Reformation" of Dimersol Oligomerization Product

A Dimersol feed-product from propylene containing about 82% hexenes, 12% nonenes and 6% higher oligomers was fed up-flow at a liquid hourly space velocity of about $5h^{-1}$ through a fixed-bed reactor containing 10 cc of the catalyst prepared similar to that described above (about 12.4%w Ta) at about 200° C. and about 500 psig. The product of the above catalytic reformation was separated by distillation into a $C_9$ olefin portion and a $C_{12}$ olefin portion.

A $C_8$ fraction was separated by distillation from a Dimersol feed-product from butylene. This $C_8$ olefin was reformed as described above.

Conversion of Olefin to Alcohol

The above-noted $C_8$ olefin portion, $C_9$ olefin portion and $C_{12}$ olefin portion were converted to alcohols by the following process.

To a 300 ml autoclave were added 110 of olefin, 1.38 g of cobalt octoate, 0.84 g of KOH/ethanol (26.7%w KOH/ethanol), and 1.32 g of (n-Bu)$_3$P. The autoclave was sealed, flushed twice with nitrogen and then pressureized with syngas, (2.1/1, $H_2$/CO). The autoclave was heated to 175° C. for the $C_8$ and $C_9$ olefins and 200° C. for the $C_{12}$ olefin and a final pressurization to 1150 psig was performed. The reaction was stirred at 1200 rpm and maintained at 1150 psig. The reaction was run for about 21 hours. After reaction the acutoclave was cooled, the contents were removed and the alcohol separated by distillation.

Adipate Production

To a 1-l Erlenmeyer flask containing 1.8 moles of alcohol was added, portion-wise, 0.9 moles of adipoyl chloride. The adipoyl chloride wad added at such a rate as to maintain the temperature below 200° C. Intermittant cooling of the flask in an ice bath was necessary to accomplish this. The contents of the flask were stirred for 2 hours after the addition of adipoyl chloride had been completed. Then, de-ionized water, one-quarter of the reaction volume, was added; the organic layer was separated, dried over alumina, and filtered. The diester was then distilled under vacuum. The diester made from the $C_9$ alcohol distilled between 440°–500° C. (adjusted to atmospheric pressure). The diester made from the $C_{10}$ alcohol distilled between 500°–520° C. (adjusted to atmospheric pressure). The diester made from the $C_{13}$ alcohol distilled between 521°–546° C. (adjusted to atmospheric pressure). The analysis by mass spectrometry confirmed that the products were the diesters indicated below.

Viscosity, viscosity index, pour point and flash point were measured for the above described adipates prepared according to the invention. Results are given below in the table. For comparison purposes the last column of the table list values for the same properties for adipates prepared from conventional oxo alcohols. These literature values are taken from SRI International's Process Economics Program Report No. 125, Synthetic Lubricants, page 148, May 1979.

| Adipate | This Invention | Literature |
| --- | --- | --- |
| Di-nonyl | | |
| Kinematic viscosity (a) | 3.23 | 2.38 |
| Viscosity index (b) | 148 | 120 |
| Pour point, °F. (c) | −60 | −75 |
| Flash point, °F. (d) | 455 | 390 |
| Di-tridecyl | | |
| Kinematic viscosity (a) | 5.25 | 5.53 |
| Viscosity index (b) | 145 | 150 |
| Pour point, °F. (c) | −65 | −65 |
| Flash point, °F. (d) | 505 | 450 |
| Di-decyl | | |
| Kinematic viscosity (a) | 3.47 | 3.56 |
| Viscosity index (b) | 150 | 148 |
| Pour point, °F. (c) | −65 | −80 |

-continued

| Adipate | This Invention | Literature |
|---|---|---|
| Flash Point, °F. (d) | 465 | 425 |

(a) Test method: ASTM D-445
Values are in cSt @ 210° F. for the literature values and 100° C. for this invention.
(b) Test method: ASTM D-2270
(c) Test method: ASTM D-97
The sample of this invention still flowed at −65° F.
(d) Test method: ASTM D-92

I claim:

1. An process for the production of dialkyl adipate lubricant compositions which process comprises:
    (a) contacting at least a portion the reaction product of the liquid phase oligomerization of propylene and/or butylene containing a $C_8$ olefin component, a $C_9$ olefin component and/or a $C_{12}$ olefin component, which reaction product was formed by reacting propylene and/or butylene in the presence of a catalyst formed by reacting a nickel compound with a hydrocarbyl aluminum halide, with a reforming catalyst comprising pentavalent tantalum, halogen, oxygen and an inorganic oxide substrate wherein at least one valence of tantalum is bound to oxygen which is bound to the substrate, at least one valence of the tantalum is bound to halogen and the remaining tantalum valences are bound to halogen and/or oxygem which may or may not be bound to the substrate, said contact taking place at a temperature ranging from about 25° C. to about 300° C.,
    (b) separating from the reaction mixture of (a) into a desired $C_8$ olefin component, a $C_9$ olefin component and/or a $C_{12}$ olefin component,
    (c) hydroformylating the desired $C_8$ olefin component, the $C_9$ olefin component and/or the $C_{12}$ olefin component to produce a desired $C_9$ alcohol component, a $C_{10}$ alcohol component and/or a $C_{13}$ alcohol component,
    (d) reacting the desired $C_9$ alcohol component, the $C_{10}$ alcohol component and/or the $C_{13}$ alcohol component with adipic acid or a suitable derivative of adipic acid to produce the corresponding adipate, and
    (e) separating the desired di-isononyl adipate, the di-decyl adipate and/or the di-tridecyl adipate from the reaction products of (d).

2. The process of claim 1, where, in said reforming catalyst of step (a), the inorganic oxide substrate is silica, alumina, silica-alumina, zeolite, open lattice clay or mixtures thereof.

3. The process of claim 1, where, in said reforming catalyst of step (a), the inorganic oxide substrate has a major component of silica, or alumina or a mixture hereof and the halogen is chloride, fluoride or a mixture thereof.

4. The process of claim 1, wherein step (a) is carried out at a temperature ranging from about 100° C. to about 250° C.

* * * * *